United States Patent

Tsinker et al.

[11] 4,130,559
[45] Dec. 19, 1978

[54] METHOD FOR THE PREPARATING OF 6-AMINOPENICILLINIC ACID DERIVATIVES

[76] Inventors: Maia G. Tsinker, ulitsa Amiriana 34, kv. 13; Julya Z. Ter-Zakharian, ulitsa Tumaniana 5, kv. 6; Shushanik G. Oganian, ulitsa Khandzhiana 43, kv. 8; Aram R. Ovakimian, ulitsa Alabiana 39, kv. 47; Shushanik L. Mndzhoian, ulitsa Sundukiana, 1, kv. 2, all of Erevan, U.S.S.R.; Armenak L. Mndzhoian, deceased, late of Erevan, U.S.S.R.; by Alza A. Mndzhoian, administratrix, ulitsa Barekamutina, 118, Kv. 24, Erevan, U.S.S.R.

[21] Appl. No.: 777,631

[22] Filed: Mar. 15, 1977

Related U.S. Application Data

[63] Continuation of Ser. No. 687,211, May 17, 1976, abandoned, which is a continuation of Ser. No. 566,824, Apr. 10, 1975, abandoned.

[51] Int. Cl.² .......................................... C07D 499/46
[52] U.S. Cl. .................................. 260/239.1; 424/271
[58] Field of Search ...................................... 260/239.1

[56] References Cited

U.S. PATENT DOCUMENTS 3,433,784    3/1969    Long et al. ...................... 260/239.1

FOREIGN PATENT DOCUMENTS 633397    11/1963    Belgium ............................... 260/239.1

OTHER PUBLICATIONS

Kirk-Othmer, Encyclopedia of Chemical Technology, vol. 14, 2nd ed., p. 698.

*Primary Examiner*—Gerald A. Schwartz
*Attorney, Agent, or Firm*—Holman & Stern

[57] ABSTRACT

6-aminopenicillanic acid derivatives characterized by the general formula

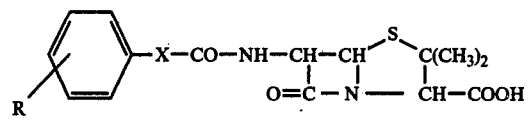

wherein R = H, alkoxy group of normal and iso-structure having 1 to 4 carbon atoms,

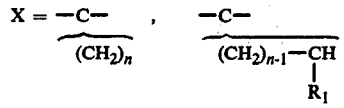

wherein n = 4, 3, 2,
$R_1$ is lower alkyl, aryl, halogen, $NH_2$, $NO_2$, OH, are prepared by acylating 6-aminopenicillanic acid with an acylating agent of the formula

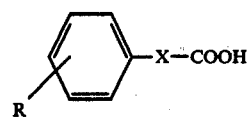

wherein R and X have the above-mentioned significance.

1 Claim, No Drawings

METHOD FOR THE PREPARATING OF 6-AMINOPENICILLINIC ACID DERIVATIVES

This is a continuation of application Ser. No. 687,211, filed May 17, 1976, now abandoned which in turn is a continuation of Ser. No. 566,824 filed Apr. 10, 1975, now abandoned.

BACKGROUND OF THE INVENTION

The present invention relates to heterocyclic compounds, and more particularly, to methods for the preparation of new 6-aminopenicillanic acid derivatives.

These compounds belongs to the group of semisynthetic penicillins. Known semisynthetic penicillins and methycillin, ampicillin, and oxacillin used in medical practice do not possess all of the desired properties, namely, a wide-range efficiency and combined acid- and penicillinase resistance. Thus, methycillin, while being penicillinase resistant, is not acid-resistant so that changes in various tissues and organs (especially in kidneys) occur after prolonged usage thereof.

In addition, the methods for preparing methycillin, as well as other preparations, are complicated and require many stages. The above-mentioned compounds are prepared by acylating 6-aminopenicillanic acid with acylating agents, such as 2,6-dimethoxy-benzoic acid, α-amino benzoic acid and phenylisoxasolyl carboxylic acid. These acylating agents require, in turn, a complicated synthesis process which cannot give a good yield of the desired product.

SUMMARY OF THE INVENTION

It is therefore an object of the invention to provide a new semisynthetic penicillin which combines both acid- and penicilinase resistance and a method for making the new semi-synthetic penicillin by acylating 6-amino penicillanic acid using more readily available acylating agents.

The above object is accomplished by the provision of 6-aminopenicillanic acid derivatives having, according to the invention, the general formula

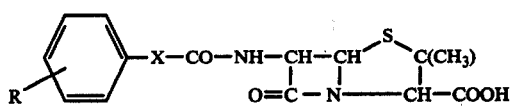

wherein R = H, normal and iso-strcuture alkoxy groups having 1 to 4 carbon atoms,

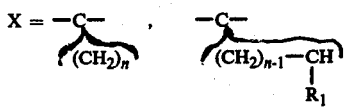

wherein n = 4, 3, 2,
R₁ is lower alkyl, aryl, halogen, NH₂, NO₂, or OH.

These 6-aminopenicillanic acid derivatives have not been disclosed in the literature and are novel.

The above-described crystalline derivatives are melted with decomposition, are well-soluble in ester, insoluble in water and readily convertible into respective salts when treated with a solution of an alkali metal bicarbonate.

Biological activity of these derivatives was studied using sodium salts thereof. They are active with respect to grampositive microorganisms. The penicillins obtained according to the invention are more active than benzylpenicillin against stable penicillinase-producing staphylococcs.

All compounds exhibit a certain degree of stability against the action of staphylococc penicillinase. The insertion of alkoxy radicals in various positions of the benzene ring results in a reduced stability of an unsubstituted derivative. However, when considered dynamically, they remain stable against penicillinase during a 4 hour long inactivation.

The penicillins are more stable than benzylpenicillin having a half-life period of 2.1 minutes in the conditions of our experiments. The insertion of alkoxy groups in various positions of benzene ring results in an improved acid resistance.

All derivatives have low toxicity. They are well tolerated when administered by a single intravenous injection in albine mice at a dose of 1500–2500 mg/kg.

According to the invention, there is provided a method for the preparation of 6-aminopenicillanic acid derivatives comprising acylating 6-aminopenicillanic acid with an agent of the formula

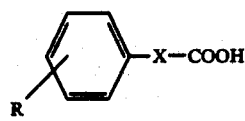

wherein R = H, alkoxy group of normal and iso-structure having 1 to 4 carbon atoms,

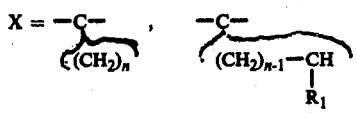

wherein n = 4, 3, 2,
R₁ is lower alkyl, aryl, halogen, NH₂, NO₂, or OH.

The above-mentioned reactants are used in stoichiometric quantities in the medium of an organic solvent inert with respect to the starting reactants.

In acylating 6-aminopenicillanic acid with an agent wherein

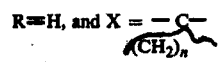

the reaction is conducted in the presence of sodium bicarbonate,. When R is represented by alkoxy groups of normal and iso-structure having 1 to 4 carbon atoms, the reaction is conducted in the presence of triethylamine and ethylchloroformiate.

The acylation reaction is conducted under normal conditions, that is under normal pressure and at room temperature.

The above-mentioned acylating agents may be obtained by conventional methods, such as by hydrolysis of nitriles under heating in an organic solvent in the presence of an alkali agent.

DESCRIPTION OF THE PREFERRED EMBODIMENTS

The invention will be better understood from the following specific examples.

EXAMPLE 1

1-Phenylcyclopentyl-1-Penicillin

To a solution of 20.8 g (0.1 mol) of 1-phenylcyclopentane-1-carboxylic acid chloroanhydride in 200 ml of abs. acetone, there was added, with stirring and cooling at 0° C for 1 hour, a solution of 21.6 g (0.1 mol) of 6-aminopenicillanic acid and 25 g of sodium bicarbonate in a mixture of 450 ml of water and 200 ml of acetone. The reaction mixture was stirred for 1 hour more with cooling and for 4 hours at room temperature and was then extracted twice with ether. The ether extract was separated. The aqueous layer was cooled at 5°-7° C, 100 ml of ether were added under stirring, and the mixture was then acidified with 1N hydrochloric acid to pH 2.0. The ether layer was then separated, and the acidified aqueous layer was additionally extracted with ether. The ether extracts added together were washed with ice-cold water and shaken with anhydrous sodium sulphate. Penicillin was extracted from the ether extract by adding, stepwise, an 8% aqueous solution of sodium bicarbonate to pH 6.5 – 7 in the aqueous layer. The latter is then separated, extracted with ether and subjected to lyophilic drying. The crystalline precipitate was triturated with abs. ether. The yeild of the sodium salt was 29.7 g, that is 72.5% of the theoretical value. A small quantity of the sodium salt was converted into penicillin acid, m.p. 114°-116° C (Table 1, compound I).

EXAMPLE 2

1-(n-Ethoxyphenyl)Cyclopentyl-1-Penicillin

To a solution of 4.68 g (0.02 mol) of 1-(n-ethoxyphenyl) cyclopentane-1-carboxylic acid in 60 ml of abs. acetone, there were added, under stirring and cooling at 0° C, 2.4 g (0.024 mol) of triethylamine in 40 ml of abs.acetone and 3 g (0.028 mol) of ethylchloroformiate in 20 ml of abs.acetone. The mixture was stirred for 30 minutes at 0° C and for 2 hours at room temperature, and subsequently, it was filtered.

Table 1

| Compound | R | X | Yield (%) | Melting Point (° C) | Analysis (%) N | S |
|---|---|---|---|---|---|---|
| I | H | =C=(CH$_2$)$_4$ | 72.5 | 114–115 | 7.07 | 8.12 |
| II | o-CH$_3$O | " | 69.3 | 132–133 | 6.46 | 7.39 |
| III | o-C$_2$H$_5$O | " | 73.6 | 114–116 | 6.21 | 7.35 |
| IV | o-C$_3$H$_7$O | " | 71.8 | 88–90 | 6.55 | 7.45 |
| V | o-iso-C$_3$H$_7$O | " | 64.2 | 123–125 | 6.56 | 7.52 |
| VI | o-C$_4$H$_9$O | " | 63.6 | 84–86 | 6.28 | 7.19 |
| VII | M-CH$_3$O | " | 71.5 | 109–110 | 6.40 | 7.46 |
| VIII | M-C$_2$H$_5$O | " | 60.9 | 99–101 | 6.28 | 7.25 |
| IX | M-C$_3$H$_7$O | " | 65.4 | 105–107 | 6.37 | 7.34 |
| X | m-iso-C$_3$H$_7$O | " | 72.5 | 84–86 | 6.15 | 7.48 |
| XI | M-C$_4$H$_9$O | " | 70.1 | 102–104 | 6.22 | 6.77 |
| XII | n-CH$_3$O | " | 59.7 | 98.9 | 6.43 | 7.76 |
| XIII | n-C$_2$H$_5$O | " | 64.8 | 128–130 | 6.23 | 7.70 |
| XIV | n-C$_3$H$_7$O | " | 65.6 | 112–114 | 6.20 | 6.95 |
| XV | p-iso-C$_3$H$_7$O | " | 66.2 | 106–108 | 6.54 | 7.25 |
| XVI | n-C$_4$H$_9$O | " | 62.4 | 118–120 | 6.30 | 6.75 |

[1]System: m-butyl alcohol-water-acetone-ether (14:4.5:4.5:5)
[2]Temperature 37° C, pH 1.3.

| Brutto Formula | Theory (%) N | S | $R_f$[1] | $[\alpha]_D^{20}$ (C water 0.1) | $T$[2] 2 (minutes) | Max. tolerated dose (mg/kg) |
|---|---|---|---|---|---|---|
| C$_{20}$H$_{24}$N$_2$O$_4$S | 7.21 | 8.24 | 0.72 | 212.7 | 26.0 | 500 |
| C$_{21}$H$_{26}$N$_2$O$_5$S | 6.69 | 7.66 | 0.68 | 186.5 | 187.0 | 2000 |
| C$_{22}$H$_{28}$N$_2$O$_5$S | 6.48 | 7.41 | 0.64 | 186.5 | 102.1 | 1000 |
| C$_{23}$H$_{30}$N$_2$O$_5$S | 6.27 | 7.18 | 0.66 | 155.4 | 14.9 | 1500 |
| C$_{23}$H$_{30}$N$_2$O$_5$S | 6.27 | 7.18 | 0.63 | 186.5 | 10.3 | 1000–1500 |
| C$_{24}$H$_{32}$N$_2$O$_5$S | 6.08 | 6.96 | 0.70 | 186.5 | 14.8 | 1000 |
| C$_{21}$H$_{26}$N$_2$O$_5$S | 6.69 | 7.66 | 0.66 | 167.8 | 287.8 | 2500 |
| C$_{22}$H$_{28}$N$_2$O$_5$S | 6.48 | 7.41 | 0.58 | 186.5 | 189.4 | 1500 |
| C$_{23}$H$_{30}$N$_2$O$_5$S | 6.27 | 7.18 | 0.74 | 155.4 | 222.0 | 1500 |
| C$_{23}$H$_{30}$N$_2$O$_5$S | 6.27 | 7.18 | 0.67 | 188.5 | 25.9 | 1500 |
| C$_{24}$H$_{32}$N$_2$O$_5$S | 6.08 | 6.96 | 0.61 | 155.4 | 277.7 | 2000 |
| C$_{21}$H$_{26}$N$_2$O$_5$S | 6.69 | 7.66 | 0.69 | 185.9 | 163.0 | 2000 |
| C$_{22}$H$_{28}$N$_2$O$_5$S | 6.48 | 7.41 | 0.75 | 185.9 | 99.2 | 1500 |
| C$_{23}$H$_{30}$N$_2$O$_5$S | 6.27 | 7.18 | 0.72 | 159.4 | 88.9 | 1500 |
| C$_{23}$H$_{30}$N$_2$O$_5$S | 6.27 | 7.18 | 0.71 | 185.9 | 160.0 | 1500 |
| C$_{24}$H$_{32}$N$_2$O$_5$S | 6.08 | 6.96 | 0.73 | 212.5 | 43.2 | 1500 |

The filtrate was added to a mixture containing 5.6 g (0.026 mol) of 6-aminopenicillanic acid in 120 ml of acetone and 100 ml of 2.5% solution of sodium bicarbonate. The mixture was stirred for 4 hours, then 100 ml of water were added, and the major part of acetone was distilled off in vacuum. The residue was extracted with ether, the aqueous layer was acidified with 1N hydrochloric acid to pH 2.0 with cooling and stirring. The isolated penicillin-acid was extracted with ethyl acetate. The extracts were than added together, washed with water for 20 minutes, and shaken with 5 g of activated charcoal and anhydrous sodium sulphate. The ethyl acetate solution was then filtered, and a part thereof was kept for isolating the acid which was recrystallized from petroleum ether. The remaining part was treated with an 8% solution of sodium bicarbonate to pH 7.0 in the aqueous layer. The aqueous layer was then washed with ether and lyophilized. The yield was 6.6 g, that is 73.6% of the theoretical value (sodium salt). The remaining penicillins with p- alkoxy residues were prepared in the similar manner (Table 1, compounds XII XIV, XV, XVI).

EXAMPLE 3

1-(m-propoxyphenyl)Cyclopentyl-1-Penicillin

To a solutin of 4.96 g (0.02 mol) of 1(m-propoxyphenyl) cyclopentane-1-carboxylic acid in 60 ml of abs.acetone cooled at 0° C, there were added, with stirring 2.4 g (0.02 mol) of triethylamine in 40 ml of abs.acetone and 3 g (0.028 mol) of ethylchloroformiate in 20 ml of abs. acetone. The stirring continued for 30 minutes more at 0° C and for an additional 2 hours at room temperature. The mixture was then filtered, and the filtrate was added to a mixture of 120 ml of an aqueous solution of 0.02 mol of 6-aminopenicillanic acid and 9 g of sodium bicarbonate in 100 ml of acetone. The mixture was stirred for 3 hours and extracted with ether. The aqueous layer was then separated, acidified with 1N hydrochloric acid at 6°-7° C to pH 2.0 and extracted with ether. The extract was washed with ice-cold water, shaken with anhydrous sodium sulphate and charcoal, and filtered, whereafter the filtrate was alkalized with an 8% solution of sodium bicarbonate to pH 6.5–7.0. The aqueous layer was separated, extracted with ether and subjected to lyophilic drying. 6.12 g of sodium salt were obtained which represented 65.4% of the theoretical value. A part of the sodium salt was converted into penicillin-acid for determination of some physical and chemical characteristics. Melting point of the acid was 105°-107° C. All remaining penicillins with m-alkoxy residues were obtained in the similar manner (Table 1, compounds VII, VIII, X, XI).

EXAMPLE 4

1-(o-Butoxyphenyl)Cyclopentyl-1-Pencillin

A solution of 5.24 g (0.02 mol) of 1-(o-butoxyphenyl)-cyclopentane-1-carboxylic acid in 60 ml of abs. acetone was cooled at 0° C, after which 2.4 g (0.02 mol) of triethylamine in 20 ml of abs. acetone were added, and subsequently 3 g (0.028 mol) of ethylchloroformiate in 20 ml of abs. acetone were added dropwise with stirring. The mixture was stirred for 30 minutes more at 0° C, then for an additional 2 hours at 20° C. The mixture was next filtered, and the filtrate was added to 180 ml of an aqueous solution of 0.02 mol of 6-aminopenicillanic acid and 9 g of sodium bicarbonate in 150 ml of acetone. The mixture was stirred for 3 hours and extracted with ether. The aqueous layer was then separated, acidified with 1N hydrochloric acid at 6°-7° C to pH 2.0 and extracted with ether. The extract was washed with ice-cold water, shaken with anhydrous sodium sulphate and charcoal and filtered, and the filtrate was alkalized with an 8% solution of sodium bicarbonate to pH 6.5–7.0. The aqueous layer was then separated, extracted with ether and subjected to lyophilic drying. The crystalline precipitate was triturated with abs. ether. The yield of the sodium salt was 6.13 g, that is 63.6% of the theoretical value. The melting point of penicillin-acid was 84°–86° C. The remaining penicillins with c-alkoxy residues were prepared in the similar manner (Table 1, compounds II, III, IV, V).

EXAMPLE 5

1-Alkoxyphenyl-Cyclopropyl-1-Penicillins

To a solution of 0.02 mol of a respective starting acid in 50 ml of abs. acetone at 0° C and with stirring, there were added a solution of 2.4 g (0.024 mol) of triethylamine in 25 ml of abs. acetone and 3 g (0.028 mol) of chlorocarbonic ethyl ester in 20 ml of abs. acetone. The mixture was stirred for 30 minutes with cooling and then for 2 hours at room temperature. The precipitate was filtered off, and the filtrate was added with stirring to a mixture of a solution of 5.6 g (0.026 mol) of 6-aminopenicillanic acid in 100 ml of acetone and 200 ml of 2.5% solution of sodium bicarbonate. The mixture was stirred for 4 hours and then extracted with ether. The ether extracts were separated, and the aqueous layer was then acidified with 1N hydrochloric acid at 7°–10° C to pH 2.5–3. The isolated penicillin was extracted with ether. The ether extracts were then washed with ice-cold water and shaken with 5 g of activated charcoal and with anhydrous sodium sulphate. The ether solution was filtered, and a part thereof was kept for isolating acids which were recristallized from petroleum ether. The other part was treated with an 8% solution of sodium bicarbonate to pH 7.0 in the aqueous layer. The aqueous layer was then separated, washed with ether and lyophilized. The respective data are given in Table 2.

EXAMPLE 6

1-Alkoxyphenyl-Cyclobutyl-1-Penicillins

To a solution of 0.02 mol of a respective 1-alkoxyphenyl-cyclobutane carboxylic acid in 50 ml of abs. acetone at 0° C and with stirring there were added a solution of 2.4 g (0.024 mol) of triethylamine in 25 ml of abs. acetone and 3 g of chlorocarbonic ethyl ester in 20 ml of abs. acetone. The mixture was stirred for 30 minutes with cooling and then for 2 hours at room temperature. The precipitate was filtered off, and the filtrate was added with stirring to a mixture of a solution of 5.6 g (0.026 mol) of 6-aminopenicillanic acid in 100 ml of acetone and 200 ml of 2.5% solution of sodium bicarbonate. The mixture was stirred for 4 hours and was then extracted with ether. The ether extracts were separated, and the aqueous layer was acidified with 1N hydrochloric acid at 7°–10° C to pH 2.5–3. The isolated penicillin was extracted with ether. The ether extracts were washed with ice-cold water and then shaken with 5 g of activated charcoal and anhydrous sodium sulphate. The ether solution was filtered, and a part thereof was kept for isolating acids which were recristallized from petroleum ether. The remaining part was treated with an 8% solution of sodium bicarbonate to pH 6.5–7 in the aqueous layer. The aqueous layer was then separated, washed with ether and lyophilized. The respective data are given in Table 3.

Penicillin derivatives of substituted cycloalkane carboxylic acids were synthesized in a similar manner.

The utility of the penicillins having the above-described structures were shown by studying their biological properties.

Table 2

| Compound | R | X | Yield (%) | Melting Point (° C) | Analysis (%) N | Analysis (%) S | Brutto Formula | Theory (%) N | Theory (%) S | $R_f^{(1)}$ | $\frac{\tau^{(2)}}{2}$ (minutes) | Max. Tolerated Dose (mg/kg) |
|---|---|---|---|---|---|---|---|---|---|---|---|---|
| I | H | =C< (CH$_2$)$_2$ | 62.5 | 116–118 | 7.60 | 8.80 | C$_{18}$H$_{20}$N$_2$O$_4$S | 7.77 | 8.89 | 0.72 | 9.9 | 1500 |
| II | o-CH$_3$O | " | 59.1 | 120–122 | 7.35 | 8.16 | C$_{19}$H$_{22}$N$_2$O$_5$S | 7.17 | 8.21 | 0.68 | 5.0 | 2000 |
| III | o-C$_2$H$_5$O | " | 58.2 | 126–128 | 7.15 | 8.26 | C$_{20}$H$_{24}$N$_2$O$_5$S | 6.92 | 7.90 | 0.71 | 6.0 | 500 |
| IV | o-C$_3$H$_7$O | " | 60.8 | 100–102 | 6.91 | 7.80 | C$_{21}$H$_{26}$N$_2$O$_5$S | 6.69 | 7.66 | 0.72 | 5.8 | 500 |
| V | o-iso-C$_3$H$_7$O | " | 58.1 | 116–118 | 6.84 | 7.93 | C$_{21}$H$_{26}$N$_2$O$_5$S | 6.69 | 7.66 | 0.75 | 6.0 | 500 |
| VI | o-C$_4$H$_9$O | " | 61.4 | 96–98 | 6.75 | 7.57 | C$_{22}$H$_{28}$N$_2$O$_5$S | 6.47 | 7.41 | 0.72 | 5.2 | 500 |
| VII | M-CH$_3$O | " | 52.1 | 114–116 | 6.90 | 8.12 | C$_{19}$H$_{22}$N$_2$O$_5$S | 7.17 | 8.21 | 0.69 | 7.2 | 1500 |
| VIII | M-C$_2$H$_5$O | " | 57.4 | 88–90 | 7.01 | 7.95 | C$_{20}$H$_{24}$N$_2$O$_5$S | 6.92 | 7.90 | 0.72 | 7.3 | 1500 |
| IX | M-C$_3$H$_7$O | " | 60.2 | 105–107 | 6.85 | 7.96 | C$_{21}$H$_{26}$N$_2$O$_5$S | 6.69 | 7.66 | 0.76 | 14.5 | 1500 |
| X | m-iso-C$_3$H$_7$O | " | 58.1 | 80–82 | 6.45 | 7.31 | C$_{21}$H$_{26}$N$_2$O$_5$S | 6.69 | 7.66 | 0.73 | 10.5 | 500 |
| XI | M-C$_4$H$_9$O | " | 59.3 | 84–86 | 6.32 | 7.72 | C$_{22}$H$_{28}$N$_2$O$_5$S | 6.47 | 7.41 | 0.74 | 6.2 | 250 |
| XII | n-CH$_3$O | " | 46.2 | 103–105 | 7.13 | 7.94 | C$_{19}$H$_{22}$N$_2$O$_5$S | 7.17 | 8.21 | 0.71 | 7.3 | 2000 |
| XIII | n-C$_2$H$_5$O | " | 48.7 | 109–111 | 7.24 | 8.16 | C$_{20}$H$_{24}$N$_2$O$_5$S | 6.92 | 7.90 | 0.70 | 6.7 | 2750 |
| XIV | n-C$_3$H$_7$O | " | 50.8 | 117–119 | 6.59 | 7.58 | C$_{21}$H$_{26}$N$_2$O$_5$S | 6.69 | 7.66 | 0.78 | 19.4 | 1000 |
| XV | m-iso-C$_3$H$_7$O | " | 61.5 | 106–108 | 6.60 | 7.92 | C$_{21}$H$_{26}$N$_2$O$_5$S | 6.69 | 7.66 | 0.81 | 5.7 | 500 |
| XVI | n-C$_4$H$_9$O | " | 60.5 | 92–94 | 6.14 | 7.12 | C$_{22}$H$_{28}$N$_2$O$_5$S | 6.47 | 7.41 | 0.72 | 6.1 | 250 |

$^{(1)}$System: p-butyl alcohol-water-acetone-ether (14:4.5:4.5:5).
$^{(2)}$Temperature 37° C, pH 1.3.

Table 3

| Compound | R | X | Yield (%) | Melting Point (° C)$^{(1)}$ | Analysis (%) N | Analysis (%) S | Brutto Formula | Theory (%) N | Theory (%) S | $R_f^{(2)}$ | $\frac{\tau^{(3)}}{2}$ (minutes) | Max. Tolerated Dose (mg/kg) |
|---|---|---|---|---|---|---|---|---|---|---|---|---|
| I | H | =C< (CH$_2$)$_3$ | 52.2 | 94–96 | 7.35 | 8.44 | C$_{19}$H$_{22}$N$_2$O$_4$S | 7.48 | 8.55 | 0.86 | 86.6 | 1000 |
| II | o-CH$_3$O | " | 56.4 | 69–71 | 6.63 | 7.70 | C$_{20}$H$_{24}$N$_2$O$_5$S | 6.92 | 7.90 | 0.78 | 7.7 | 500 |
| III | o-C$_2$H$_5$O | " | 60.7 | 65.67 | 6.43 | 7.38 | C$_{21}$H$_{26}$N$_2$O$_5$S | 6.69 | 7.66 | 0.82 | 19.1 | 250 |

Table 3-continued

| Compound | R | X | Yield (%) | Melting Point (°C)[1] | Analysis (%) N | Analysis (%) S | Brutto Formula | Theory (%) N | Theory (%) S | $R_f^{(2)}$ | $\frac{\tau^{(3)}}{2}$ (minutes) | Max. Tolerated Dose (mg/kg) |
|---|---|---|---|---|---|---|---|---|---|---|---|---|
| IV | o-C$_3$H$_7$O | " | 54.9 | 112–114 | 6.85 | 7.18 | C$_{22}$H$_{28}$N$_2$O$_5$S | 6.47 | 7.41 | 0.79 | 23.0 | 500 |
| V | o-iso-C$_3$H$_7$O | " | 58.2 | 105–107 | 6.58 | 7.42 | C$_{22}$H$_{28}$N$_2$O$_5$S | 6.47 | 7.41 | 0.76 | 18.6 | 250 |
| VI | o-C$_4$H$_9$O | " | 62.4 | 80–82 | 6.27 | 7.45 | C$_{23}$H$_{30}$N$_2$O$_5$S | 6.27 | 7.18 | 0.83 | 24.9 | 1000 |
| VII | m-CH$_3$O | " | 59.1 | 77–79 | 6.29 | 8.22 | C$_{20}$H$_{24}$N$_2$O$_5$S | 6.92 | 7.90 | 0.80 | 56.9 | 1500 |
| VIII | m-C$_2$H$_5$O | " | 58.3 | 110–112 | 6.65 | 7.55 | C$_{21}$H$_{26}$N$_2$O$_5$S | 6.69 | 7.66 | 0.84 | 23.8 | 1500 |
| IX | m-C$_3$H$_7$O | " | 53.4 | 97–99 | 6.35 | 7.15 | C$_{22}$H$_{28}$N$_2$O$_5$S | 6.47 | 7.41 | 0.78 | 20.1 | 250 |
| X | m-iso-C$_3$H$_7$O | " | 49.8 | 81–83 | 6.75 | 7.21 | C$_{22}$H$_{28}$N$_2$O$_5$S | 6.47 | 7.41 | 0.77 | 17.2 | 500 |
| XI | m-C$_4$H$_9$O | " | 57.6 | 88–90 | 6.57 | 7.45 | C$_{23}$H$_{30}$N$_2$O$_5$S | 6.27 | 7.18 | 0.84 | 46.6 | 1000 |
| XII | n-CH$_3$O | " | 61.3 | 85–87 | 7.08 | 7.59 | C$_{20}$H$_{24}$N$_2$O$_5$S | 6.92 | 7.90 | 0.81 | 10.7 | 1500 |
| XIII | n-C$_2$H$_5$O | " | 62.8 | 90–92 | 6.82 | 7.82 | C$_{21}$H$_{26}$N$_2$O$_5$S | 6.69 | 7.66 | 0.82 | 189.9 | 1000 |
| XIV | n-C$_3$H$_7$O | " | 56.7 | 115–117 | 6.64 | 7.57 | C$_{22}$H$_{28}$N$_2$O$_5$S | 6.47 | 7.41 | 0.83 | 27.3 | 250 |
| XV | p-iso-C$_3$H$_7$O | " | 61.5 | 101–103 | 6.65 | 7.68 | C$_{22}$H$_{28}$N$_2$O$_5$S | 6.47 | 7.41 | 0.80 | 60.1 | 500 |
| XVI | n-C$_4$H$_9$O | " | 58.5 | 86–88 | 6.30 | 7.46 | C$_{23}$H$_{30}$N$_2$O$_5$S | 6.27 | 7.18 | 0.79 | 25.6 | 500 |

[1] Melted with decomposition.
[2] System: n-butyl alcohol:water:acetone:ether (14:4.5:4.5:5).
[3] Temperature 37° C, pH 1.3.

EXAMPLE 7

1-Alkoxyphenyl-Cyclopentyl-1-Penicillins

All compounds of this group were prepared in the form of sodium salts. Bactericidal activity, degree of hydrolysis with staphylococc penicillinase and acid resistance of the penicillins were determined.

Alkoxyphenyl-cyclopentyl penicillins were active only against gram-positive microorganisms. The resulting penicillins were more active than benzyl penicillins against stable penicillinase-producing staphylococcs (Table 4).

Phenylcyclopentyl penicillin exhibited 100% stability during the first hour after inactivation. Insertion of alkoxy radicals in various positions of the benzene ring resulted in a reduction of stability of an unsubstituted derivative. Generally, the derivatives substituted in the meta-position are somewhat more stable. The substitution of propoxy radical for iso-radical in this position is not accompanied by areduction of penicillin stability against penicillinase which is not observed in the ortho- and para-positions. During the subsequent hours of inactivation the rate of hydrolysis of penicillins slightly increases. However, even when observed in dynamics, their stability against penicillianase still persists during 4-hour-inactivation.

The penicillins are more stable than benzyl penicillin having a half-life period of 2.1 minutes under conditions of our experiments. The half-life period of an unsubstituted derivative was 26 minutes. The introduction of alkoxy group in all positions results in an improved acid resistance of an unsubstituted derivative. Compounds having a half-life period of 160–200 minutes also are a part of this group of penicillins (Table 1).

All alkoxy-substituted phenylcyclopentyl penicillins have low toxicity. They are well tolerated when admin- Table 4

| Test Microbs | Minimal Bacteriostatic Concentration (μg/ml) | | | | | | | | | | | | | | | |
|---|---|---|---|---|---|---|---|---|---|---|---|---|---|---|---|---|
| | I H | II O—CH$_3$O | III O—C$_2$H$_5$O | IV O—C$_3$H$_7$O | V O-i-C$_3$H$_7$O | VI O—C$_4$H$_9$O | VII M—CH$_5$O | VIII M—C$_2$H$_5$O | IX m-C$_3$H$_4$O | X H—i-C$_3$H$_2$O | XI H—C$_4$H$_5$O | XII n-CH$_3$O | XIII n-C$_2$H$_5$O | XIV n-C$_3$H$_4$O | XV n-i-C$_3$H$_2$O | XVI n-C$_4$H$_3$O | Benzyl Penicillin |
| Strept. pyrogenes | 0.012 | 0.78 | 0.78 | 0.39 | 0.78 | 0.39 | 0.39 | 0.39 | 0.39 | 0.19 | 0.39 | 0.048 | 0.048 | 0.048 | 0.09 | 0.048 | 0.003 |
| Staph. albus | 0.048 | 0.9 | 0.39 | 0.39 | 0.78 | 0.19 | 0.39 | 0.19 | 0.19 | 0.19 | 0.19 | 0.19 | 0.09 | 0.09 | 0.19 | 0.19 | 0.006 |
| Staph. aureus 209p | 0.048 | 0.9 | 0.78 | 0.19 | 0.39 | 0.39 | 0.39 | 0.39 | 0.39 | 0.39 | 0.39 | 0.19 | 0.19 | 0.39 | 0.19 | 0.39 | 0.012 |
| Staph. aureus 209p (adapted to benzyl-penicillin) | >500 | >500 | >500 | >500 | >500 | >500 | >500 | >500 | >500 | >500 | — | — | — | — | — | — | >500 |
| Staph. aureus (4 chemical strains) | 7.8–250 | 62.5–250 | 62.5–250 | 125–250 | 125–250 | 125–250 | 125–500 | 250–500 | 125–500 | 250–500 | 125–250 | 31.2–250 | 62.5–250 | 62.5–250 | 62.5–250 | 125–500 | 31.2–2000 |
| B.Subtitis ATCC6633 | 0.09 | 3.9 | 7.8 | 15.6 | 7.8 | 15.6 | 1.56 | 0.9 | 0.9 | 7.8 | 1.56 | 0.24 | 0.24 | 0.24 | 0.24 | 0.24 | 0.048 |
| E.typhi | 62.5 | 62.5 | 62.5 | 62.5 | 125 | 125 | — | 31.2 | 15.6 | 15.6 | — | 7.8 | 7.8 | 7.8 | 7.8 | 15.6 | 0.39 |
| Sh.dysenteriae Flexneri | 125 | 62.5 | 125 | 125 | 250 | 250 | 125 | 125 | 62.5 | 62.5 | 125 | 31.2 | 31.2 | 31.2 | 31.2 | 62.5 | 3.12 |
| E.coli O-55 | 500 | 250 | 500 | >125 | 500 | 500 | 250 | 250 | 250 | 250 | 125 | 125 | 62.5 | 125 | 25 | 125 | 31.2 |
| Prot.vulgaris | 250 | 500 | 500 | 500 | 500 | 500 | 125 | 250 | 125 | 250 | 125 | 62.5 | 62.5 | 62.5 | 62.5 | 125 | 1.56 |
| Ps.aeruginosa | >500 | >500 | >500 | >500 | >500 | >500 | >500 | >500 | >500 | >500 | — | >500 | >500 | >500 | >500 | >500 | >500 |
| Vibrion Metschnicoff | 0.24 | | 0.09 | 0.9 | 0.9 | 0.9 | 1.56 | 3.9 | 3.9 | 3.9 | 15.6 | 0.48 | 0.19 | 0.9 | 0.48 | 0.48 | 0.78 |
| Myco smegmatis | >500 | >500 | >500 | >500 | >500 | >500 | >500 | >500 | >500 | >500 | >500 | >500 | >500 | >500 | >500 | >500 | >500 | istered as a single intravenous injection in albine mices at a dose from 1500 to 2500 mg/kg. Unsubstituted derivatives are comparatively more toxic. The penicillin derivatives of cycloalkane carboxylic acids exhibit similar properties.

All penicillins exhibit a certain degree of stability against staphylococc penicillinase (Table 5).

Table 5

| R | Quantity of inactivated units of compounds under the action of 1 unit of staphylococc penicillinase |
|---|---|
| H— | 0 |
| CH₃O— | 28.8 |
| | 11 + 46.6 |
| C₂H₅O— | 20.5 |
| | 0.7 + 40.3 |

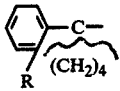

| C₃H₇O— | 20.45 |
| | 10.93 + 29.97 |
| i-C₃H₇O— | 12.0 |
| | 5.8 + 18.2 |
| C₄H₉O | 16.6 |
| | 7 + 26.2 |
| CH₃O | 14.2 |
| | 9.7 + 18.7 |
| C₂H₅O | 10.0 |
| | 3.3 + 16.7 |

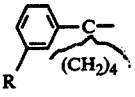

| C₃H₇O | 10.6 |
| | 1.9 + 19.3 |
| i-C₃H₇O | 27.5 |
| | 13.3 + 41.7 |
| C₄H₉O | 11.2 |
| | 1 + 21.4 |
| CH₃O | 40.3 |

Table 5-continued

| R | Quantity of inactivated units of compounds under the action of 1 unit of staphylococc penicillinase |
|---|---|
| | 28.7 + 51.9 |
| C₂H₅O | 24.9 |
| | 1 + 47.0 |

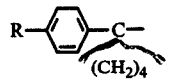

| C₃H₇O | 10.4 |
| | 1.8 + 19.0 |
| i-C₃H₇O | 9.4 |
| | 1 + 17.8 |
| C₄H₉O | 23.3 |
| | 15.0 + 31.6 |

What is claimed is:

1. 6-aminopenicillanic acid derivatives having the general formula:

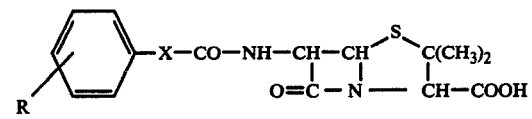

wherein R is selected from the group consisting of H and alkoxy groups of normal and iso-structure having 1 to 4 carbon atoms;
X is selected from the group consisting of

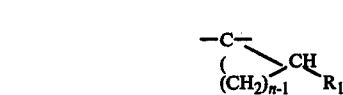

wherein n = 4, 3, 2; and
R₁ is selected from the lower alkyls, phenyl, benzyl, halogen, NH₂, NO₂, and OH.

* * * * *